US012796892B2

(12) United States Patent
Doi

(10) Patent No.: US 12,796,892 B2
(45) Date of Patent: Nov. 17, 2026

(54) MEDICAL APPARATUS AND POSITIONING METHOD FOR TREATMENT INSTRUMENT

(71) Applicant: OLYMPUS MEDICAL SYSTEMS CORP., Tokyo (JP)

(72) Inventor: Daisuke Doi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 573 days.

(21) Appl. No.: 18/124,623

(22) Filed: Mar. 22, 2023

(65) Prior Publication Data

US 2023/0301494 A1 Sep. 28, 2023

Related U.S. Application Data

(60) Provisional application No. 63/323,814, filed on Mar. 25, 2022.

(51) Int. Cl.
*A61B 1/00* (2006.01)
*A61B 1/018* (2006.01)

(52) U.S. Cl.
CPC .......... *A61B 1/00098* (2013.01); *A61B 1/018* (2013.01)

(58) Field of Classification Search
CPC ....... A61B 1/018; A61B 1/012; A61B 1/0125; A61B 1/00137; A61B 1/00098; A61B 1/0008; A61B 1/00089; A61B 1/00101; A61B 1/00105
See application file for complete search history.

(56) References Cited

U.S. PATENT DOCUMENTS

| | | | | |
|---|---|---|---|---|
| 5,460,168 | A * | 10/1995 | Masubuchi | A61B 1/00098 600/107 |
| 5,855,569 | A * | 1/1999 | Komi | A61B 10/04 604/103 |
| 9,149,173 | B2 * | 10/2015 | Scopton | A61B 1/018 |
| 10,433,717 | B1 | 10/2019 | Truckai et al. | |
| 12,022,993 | B2 * | 7/2024 | Saito | A61B 1/00042 |

(Continued)

FOREIGN PATENT DOCUMENTS

| | | |
|---|---|---|
| CN | 108135445 A | 6/2018 |
| JP | 43-003251 B | 2/1968 |

(Continued)

OTHER PUBLICATIONS

Office Action dated Dec. 25, 2025, issued in corresponding Chinese Patent Application No. 202310284065.2.

*Primary Examiner* — Ryan N Henderson
(74) *Attorney, Agent, or Firm* — Morgan, Lewis & Bockius LLP

(57) ABSTRACT

A medical apparatus comprises an insertion section inserted into a subject, a treatment instrument channel provided in the insertion section along an insertion axis extending from a proximal end to a distal end of the insertion section, a treatment instrument being inserted through the treatment instrument channel, an elastic member provided in at least a part of the treatment instrument channel, and a channel operation member for transmitting an operation force to the elastic member, and wherein the elastic member changes, according to the operation force, a sectional area of an inside of the treatment instrument channel in a direction crossing the insertion axis.

17 Claims, 14 Drawing Sheets

(56) References Cited

U.S. PATENT DOCUMENTS

| | | | | |
|---|---|---|---|---|
| 2005/0049455 | A1* | 3/2005 | Ootawara | A61B 1/01 600/107 |
| 2007/0293719 | A1* | 12/2007 | Scopton | A61B 1/00098 600/106 |
| 2017/0035277 | A1 | 2/2017 | Kucharski et al. | |
| 2020/0221931 | A1* | 7/2020 | Wilder | A61B 1/00158 |
| 2020/0297192 | A1* | 9/2020 | Hanawa | A61B 1/00133 |
| 2020/0352412 | A1* | 11/2020 | Saito | A61B 1/00042 |
| 2021/0015348 | A1 | 1/2021 | Wilder et al. | |
| 2021/0076909 | A1 | 3/2021 | Ueda et al. | |
| 2021/0121054 | A1* | 4/2021 | Ueda | A61B 50/10 |
| 2022/0211249 | A1* | 7/2022 | Kucharski | A61B 1/0008 |
| 2023/0016459 | A1* | 1/2023 | Miller | A61B 1/00098 |
| 2023/0165447 | A1* | 6/2023 | Crawford | A61B 1/00154 600/127 |
| 2023/0172435 | A1* | 6/2023 | Miller | A61B 1/00098 600/107 |
| 2023/0301498 | A1* | 9/2023 | Iwasaki | A61B 1/00091 |
| 2024/0382076 | A1* | 11/2024 | Bob | A61B 1/018 |
| 2025/0255464 | A1* | 8/2025 | Kucharski | A61B 1/018 |

FOREIGN PATENT DOCUMENTS

| | | | | |
|---|---|---|---|---|
| JP | 2001-104240 | A | | 4/2001 |
| JP | 3537180 | B2 | | 6/2004 |
| JP | 4297484 | B2 | | 7/2009 |
| JP | 2009-183389 | A | | 8/2009 |
| JP | S5636935 | A | * | 4/2010 |
| JP | 4500017 | B2 | | 7/2010 |
| JP | 2011-083329 | A | | 4/2011 |
| JP | 4836713 | B2 | | 12/2011 |
| JP | 2012-090970 | A | | 5/2012 |
| JP | 2021-166567 | A | | 10/2021 |
| JP | 2022-517104 | A | | 3/2022 |
| JP | 2022-540883 | A | | 9/2022 |
| WO | 2015/159719 | A1 | | 10/2015 |
| WO | 2020/162565 | A1 | | 8/2020 |

* cited by examiner

MEDICAL APPARATUS AND POSITIONING METHOD FOR TREATMENT INSTRUMENT

CROSS-REFERENCE TO RELATED APPLICATION

This application is based on and claims priority under 35 U.S.C. § 119 to U.S. Provisional Application No. 63/323,814, filed Mar. 25, 2022, the entire contents of which are incorporated herein by reference.

BACKGROUND

1. Field of the Disclosure

The present disclosure relates to a medical apparatus including a treatment instrument channel and a positioning method for a treatment instrument.

2. Description of Related Art

A medical apparatus such as an endoscope has been widely used in a medical field. By inserting an elongated insertion section into a subject, the endoscope can perform observation, treatment, and the like for a site to be examined. In general, the treatment for the site to be examined is performed by inserting various treatment instruments through a treatment instrument channel provided in the insertion section.

Further, in the endoscope, a component functioning as the treatment instrument channel is well known as a suction channel for suctioning out bodily fluids, cleaning liquids, biological tissue, and the like generated during the treatment. In such an endoscope, in particular, it is desirable to increase an inner diameter of the treatment instrument channel.

SUMMARY

A medical apparatus according to an aspect of the present disclosure includes: an insertion section; and a treatment instrument channel, wherein the treatment instrument channel is located in the insertion section along an insertion axis extending from a proximal end to a distal end of the insertion section, wherein the treatment instrument channel includes: an elastically deformable member, and a channel operation member coupled to the elastically deformable member for transmitting an operational force to the elastically deformable member, and wherein, in response to the operational force transmitted to the elastically deformable member by the channel operation member, the elastically deformable member changes a cross-sectional area of the treatment instrument channel in a direction intersecting the insertion axis.

A medical apparatus according to another aspect of the present disclosure includes: an insertion section; a treatment instrument channel located in the insertion section along an insertion axis extending from a proximal end of the insertion section to a distal end of the insertion section; an elastically deformable member located in at least a part of the treatment instrument channel; and a channel operation member coupled to the treatment instrument channel for transmitting an operational force to the elastically deformable member, and wherein, in response to the operational force transmitted to the elastically deformable member by the channel operation member, the elastically deformable member changes a cross-sectional area of an inside of the treatment instrument channel in a direction intersecting the insertion axis.

A positioning method for a treatment instrument using the medical apparatus according to the aspect of the present disclosure includes: inserting the treatment instrument to a predetermined position of the treatment instrument channel; and changing the cross-sectional area of the treatment instrument channel in the direction intersecting the insertion axis by operating the channel operation member.

DETAILED DESCRIPTION

In general, when an inner diameter of a treatment instrument channel is set sufficiently larger than outer diameters of shafts of various treatment instruments, the shafts of the treatment instruments easily bend on an inside of the treatment instrument channel. When such a bend of the shafts occurs, in some cases, behavior of end effectors provided at distal ends of the shafts becomes unstable and operability of the treatment instruments is deteriorated.

According to embodiments explained below, it is possible to improve operability of a treatment instrument inserted through a treatment instrument channel.

Figure 1:
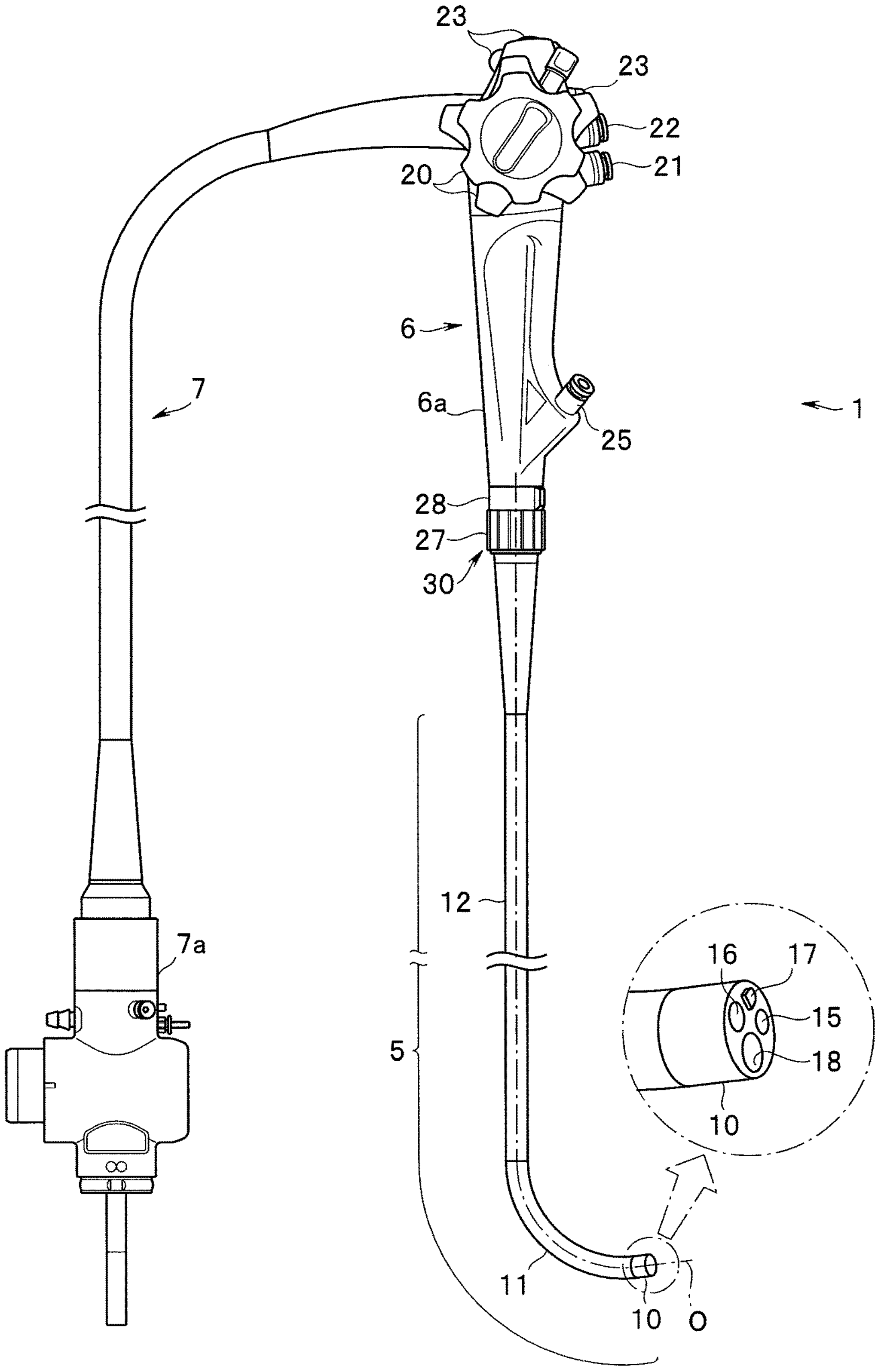
FIG. 1 relates to a first embodiment and is a schematic configuration diagram of an endoscope.

Embodiments of the present disclosure are explained below with reference to the drawings. FIG. 1 to FIG. 9 relate to a first embodiment of the present disclosure. FIG. 1 is a schematic configuration diagram of an endoscope system. Note that, in the figures used for the following explanation, scales are differentiated for each of components in order to show the respective components to recognizable degrees of sizes on the drawings. Therefore, the present disclosure is not limited to only the numbers of the components, shapes of the components, ratios of sizes of the components, and relative positional relations among the respective components described in these figures.

An endoscope 1 functioning as a medical apparatus shown in FIG. 1 is, for example, a single-use endoscope. The endoscope 1 includes an insertion section 5, an operation section 6, and a universal cable 7.

The insertion section 5 includes a distal end portion 10, a bending section 11, and a flexible tube section 12. The distal end portion 10, the bending section 11, and the flexible tube section 12 are provided in order from a distal end side along an insertion axis O extending from the distal end side to a proximal end side of the insertion section 5.

Figure 2:
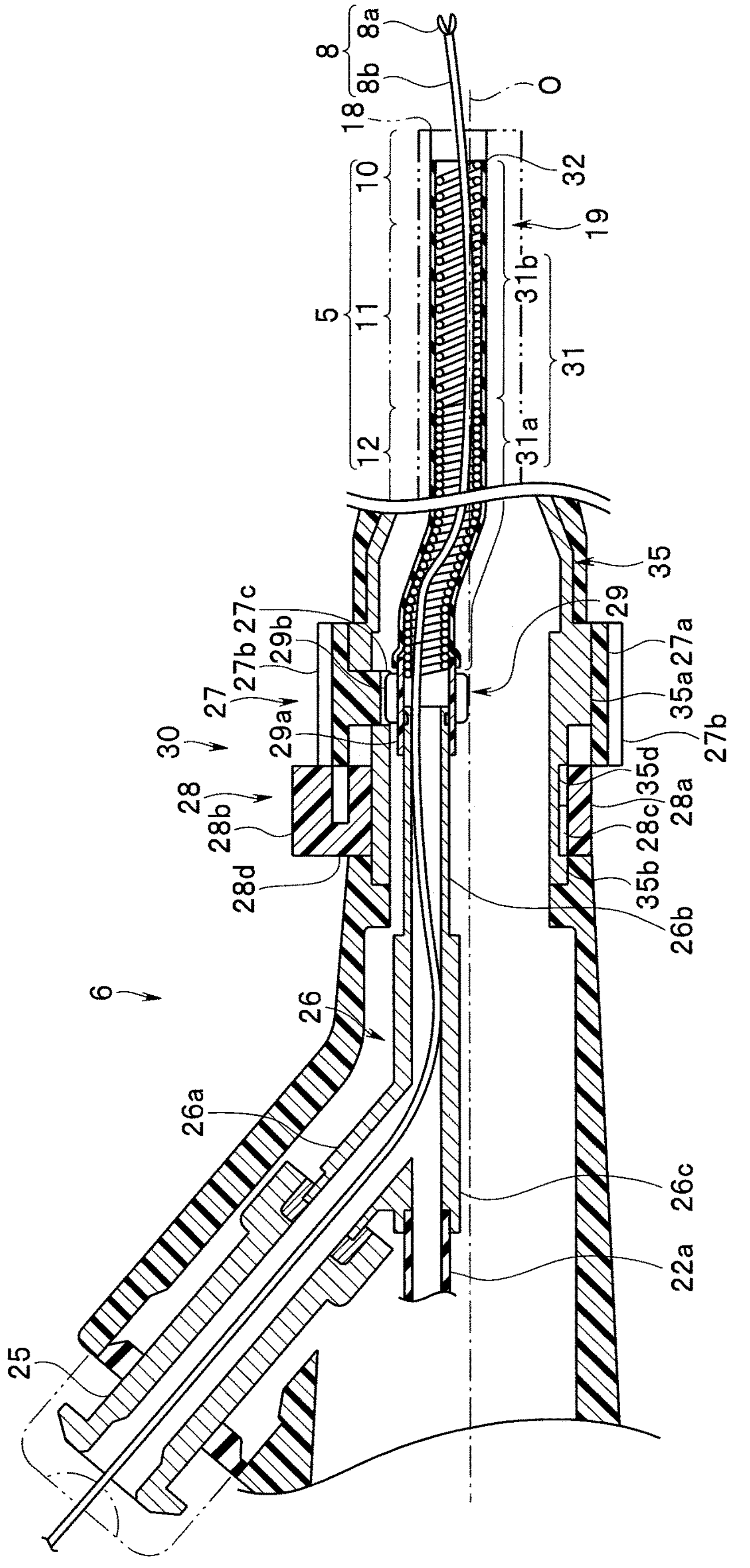
FIG. 2 relates to the first embodiment and is a main part sectional view of an operation section and an insertion section at a time when a treatment instrument channel is not reduced in diameter.
Figure 3:
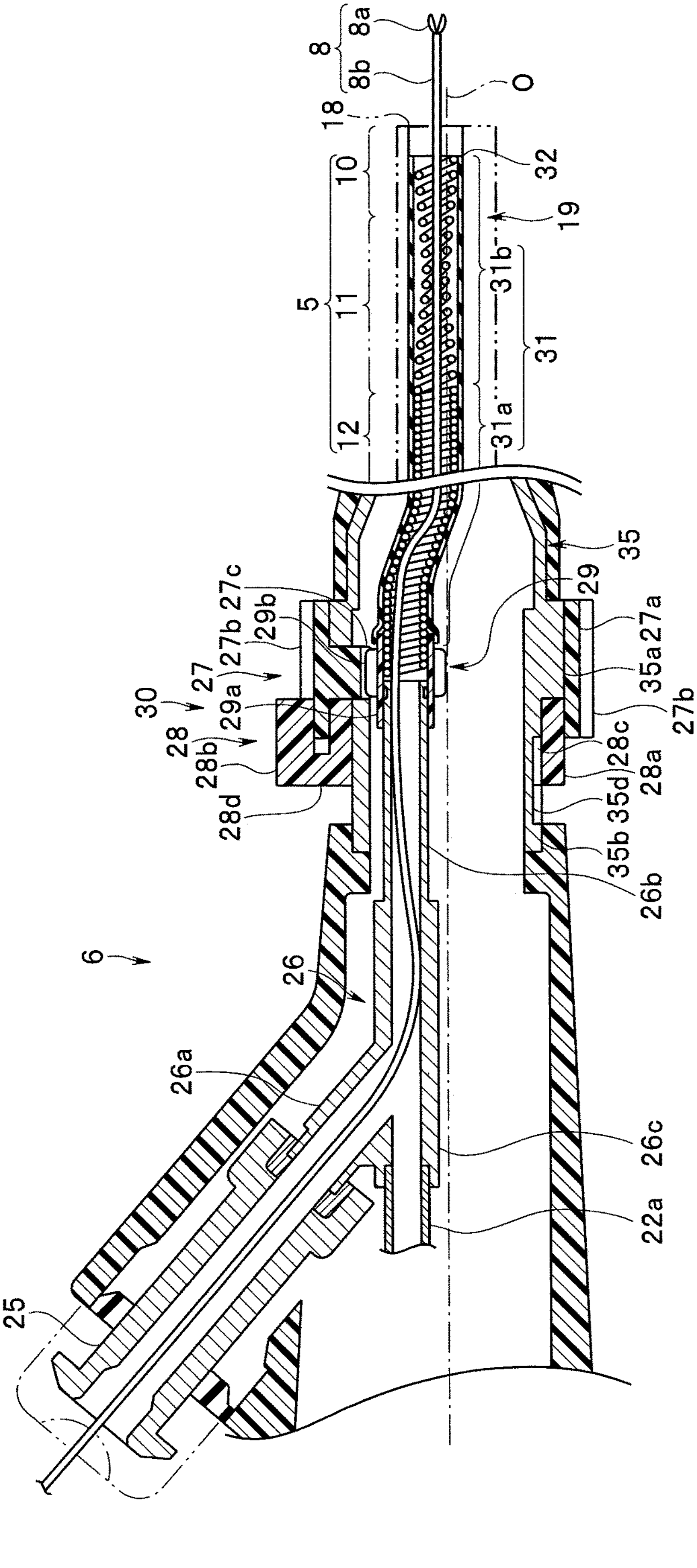
FIG. 3 relates to the first embodiment and is a main part sectional view of the operation section and the insertion section at a time when the treatment instrument channel is reduced in diameter.

The distal end portion 10 includes, for example, an illumination optical system 15 (an illumination unit), an image pickup unit 16, a nozzle 17, and a distal end side opening 18 of a treatment instrument channel 19 (see FIGS. 2 and 3).

The illumination optical system 15 irradiates a subject with, for example, illumination light transmitted from a not-shown light source apparatus through a light guide.

The image pickup unit 16 includes an image pickup optical system and an image pickup device. The image pickup device is, for example, an image sensor. The image pickup optical system forms reflected light from the subject as an optical image. The image pickup device picks up the optical image formed by the image pickup optical system and generates an image pickup signal. The image pickup signal generated by the image pickup device is outputted through a signal cable connected to the image pickup unit.

The nozzle 17 is connected to a gas feeding and liquid feeding channel (not shown) inserted through the insertion section 5. A distal end of the nozzle 17 is directed to an objective lens provided at a distal end of the image pickup optical system. Consequently, the nozzle 17 is capable of jetting, to the objective lens, gas or liquid supplied from the gas feeding and liquid feeding channel.

The distal end side opening 18 is connected to a distal end of the treatment instrument channel 19 provided on an inside of the insertion section 5 along the insertion axis O (see FIGS. 2 and 3). The distal end side opening 18 is an opening for projecting, to an outside of the distal end portion 10, a distal end side (an end effector 8*a*) of a treatment instrument 8 inserted into the treatment instrument channel 19 from the operation section 6 side. Consequently, a surgeon or the like is capable of performing various kinds of treatment for the subject. Further, the treatment instrument channel 19 also has a function of a suction conduit for suctioning out suction target objects such as bodily fluids, cleaning liquids, and biological tissue from an inside of the subject. Note that an inner diameter of the treatment instrument channel 19 also having the function of the suction conduit in this way is set sufficiently larger than an outer diameter of a shaft 8*b* of the treatment instrument 8.

For example, the bending section 11 is configured to be bendable in up, down, left, and right four directions. When the bending section 11 is bent, a direction of the distal end portion 10 changes. Consequently, an observation direction by the image pickup unit 16 changes. The bending section 11 is also bent in order to improve an insertion property of the insertion section 5 in the subject as well. Note that, although a configuration bendable in the four directions is cited as an example here, the bending section 11 may have a configuration bendable in two directions. The endoscope 1 may be a type not including the bending section 11.

The flexible tube section 12 is a flexible tube section that bends according to a shape of the subject into which the insertion section 5 is inserted. Although the flexible endoscope including the flexible tube section 12 is cited as an example of the endoscope 1 here, the endoscope 1 may be a rigid endoscope including a rigid tube section.

The operation section 6 is connected to a proximal end side of the insertion section 5. The operation section 6 includes a grasping section 6*a* that can be grasped by the surgeon or the like with a hand.

The operation section 6 includes a bending operation lever 20, a gas feeding and liquid feeding button 21, a suction button 22, a plurality of button switches 23, and the like further on the proximal end side than the grasping section 6*a*.

The bending operation lever 20 is an operation member for bending the bending section 11.

The gas feeding and liquid feeding button 21 is an operation button for performing gas feeding or liquid feeding to the objective lens of the image pickup unit 16 from the nozzle 17.

The suction button 22 is an operation button for suctioning out, through the treatment instrument channel 19, the suction target objects from the distal end side opening 18 provided at the distal end portion 10.

Operation for performing various functions of the endoscope 1 can be optionally allocated to the button switches 23. For example, operation relating to an image pickup function can be allocated to the button switches 23.

The operation section 6 includes a pipe sleeve 25 for treatment instrument insertion further on the distal end side than the grasping section 6*a*. On an inside of the operation section 6, the pipe sleeve 25 is connected to the treatment instrument channel 19 via a relay member 26 (see FIGS. 2 and 3). Consequently, the surgeon or the like is capable of inserting various treatment instruments 8 into an inside of the treatment instrument channel 19 from the pipe sleeve 25. Note that examples of the treatment instruments 8 inserted from the pipe sleeve 25 include biopsy forceps and a high-frequency snare.

The operation section 6 includes a channel operation knob 27 (ring) functioning as a channel operation member and a slider 28 functioning as a fixing member further on the distal end side than the pipe sleeve 25. The slider 28 is a fixing member capable of fixing a rotation position of the channel operation knob 27.

The channel operation knob 27 is supported by the operation section 6, for example, in a state in which the channel operation knob 27 is capable of turning around the insertion axis O. The slider 28 is supported by the operation section 6, for example, in a state in which the slider 28 is capable of advancing and retracting in an axial direction of the insertion axis O. The channel operation knob 27 and the slider 28 configure a channel operation mechanism 30 (explained below) for changing the inner diameter of the treatment instrument channel 19.

The universal cable 7 is extended from, for example, the proximal end side of the operation section 6. The universal cable 7 is a connection cable for connecting the endoscope 1 to a light source apparatus, a processor, a liquid feeding tank, a suction pump, and the like (all of which are not shown). Therefore, the light guide, the signal cable, the gas feeding and liquid feeding channel, the suction channel, and the like explained above are inserted through an inside of the universal cable 7.

An endoscope connector 7*a* is provided at an extension end of the universal cable 7. The endoscope connector 7*a* is connectable to various kinds of equipment such as the light source apparatus including a gas feeding pump, the processor, the liquid feeding tank, the suction pump, and the like (all of which are not shown).

Subsequently, configurations of the treatment instrument channel 19 and the channel operation mechanism 30 are more specifically explained with reference to FIG. 2 to FIG. 8.

The treatment instrument channel 19 in the present embodiment includes a coil 31 formed by winding an element wire of metal or the like and an outer skin 32 that covers an outer circumference of the coil 31.

The coil 31 includes a first coil section 31*a* and a second coil section 31*b* functioning as an elastic member.

The first coil section 31*a* is formed by, for example, winding an element wire at a dense pitch without a gap. The first coil section 31*a* is disposed, for example, on the inside of the operation section 6 and an inside of the flexible tube section 12 (see FIGS. 2 and 3).

The second coil section 31*b* is continuously formed on the distal end side of the first coil section 31*a* by the same element wire as the element wire forming the first coil section 31*a*. The second coil section 31*b* is formed by winding the element wire at a rougher pitch than the pitch of the first coil section 31*a*. The second coil section 31*b* is disposed, for example, on insides of the bending section 11 and the distal end portion 10 (see FIGS. 2 and 3). In other words, the second coil section 31*b* is disposed further on the distal end side than the flexible tube section 12.

The second coil section 31*b* formed by winding the element wire at the rough pitch in this way is more easily elastically deformed than the first coil section 31*a*.

Therefore, when a rotational force in a normal direction (a twisting direction) with respect to a winding direction of the element wire is inputted to the coil 31, the second coil section 31*b* reduces an inner diameter of the second coil section 31*b*. In other words, the second coil section 31*b* changes in a direction in which a sectional area of the inside of the treatment instrument channel 19 in a direction crossing the insertion axis O is reduced.

Conversely, when a rotational force in an opposite direction (a direction in which a twist is relaxed) with respect to the winding direction of the element wire is inputted to the coil 31, the second coil section 31*b* expands the inner diameter of the second coil section 31*b* to an original inner diameter. In other words, the second coil section 31*b* changes in a direction in which the sectional area of the inside of the treatment instrument channel 19 in the direction crossing the insertion axis O is enlarged to an original sectional area.

The outer skin 32 is configured by, for example, a flexible resin tube. The outer skin 32 integrally covers outer circumferences of the first coil section 31*a* and the second coil section 31*b* to thereby secure watertightness of the treatment instrument channel 19.

The distal end side of the treatment instrument channel 19 configured in this way is fixed to the distal end portion 10 in an unturnable state.

Figure 4:
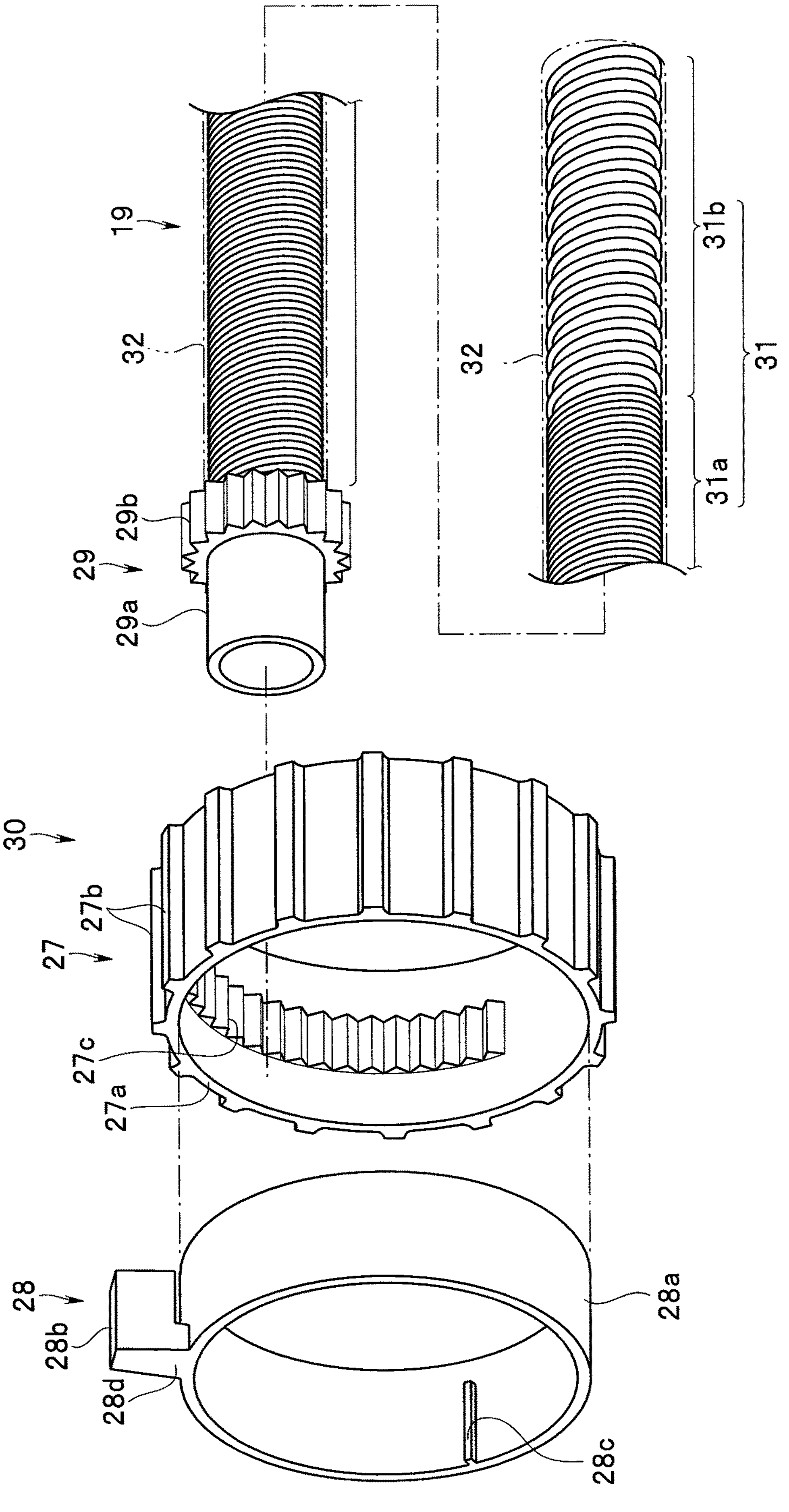
FIG. 4 relates to the first embodiment and is an exploded perspective view of a channel operation mechanism.
Figure 5:
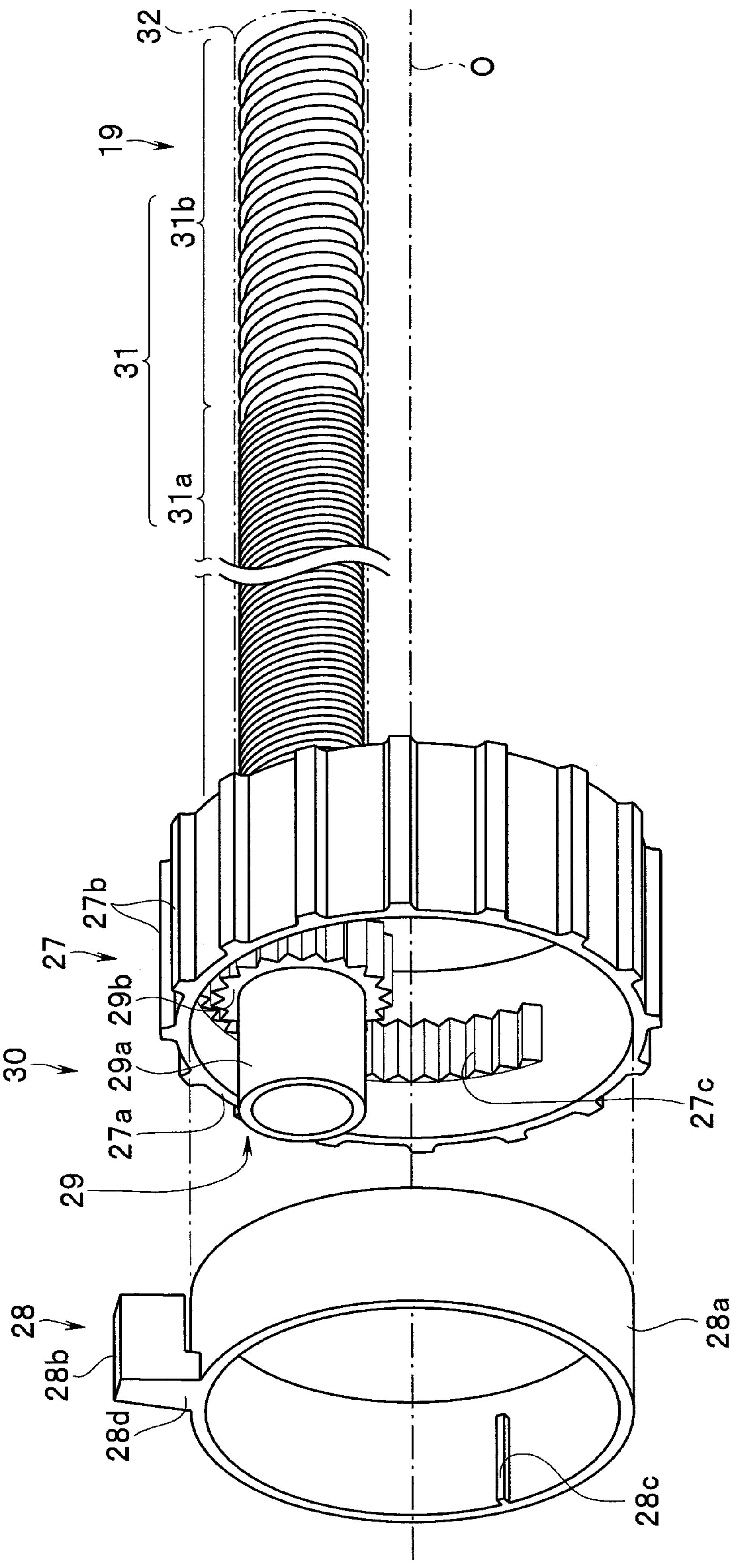
FIG. 5 relates to the first embodiment and is a perspective view of the channel operation mechanism from which a slider is detached.
Figure 6:
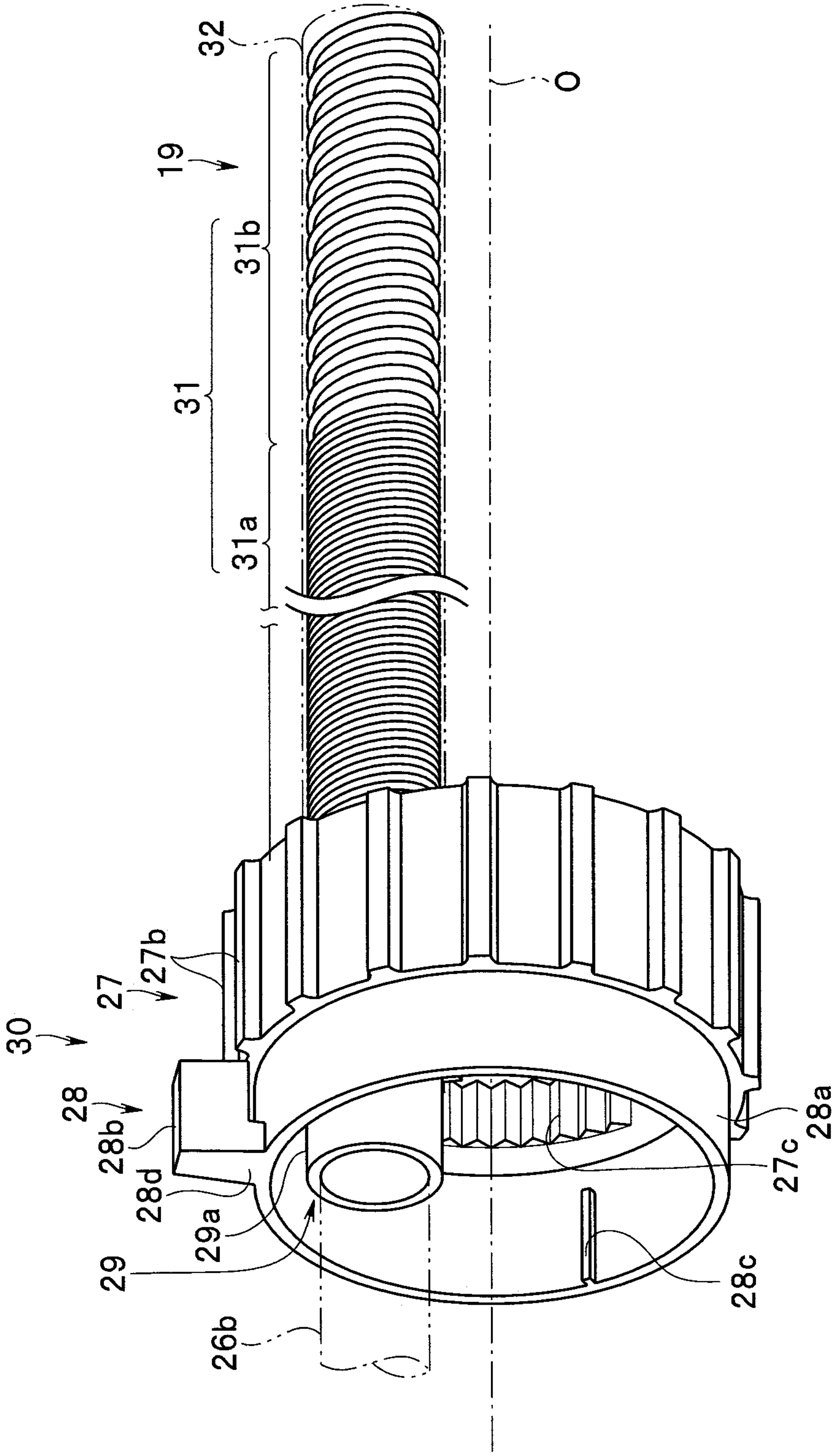
FIG. 6 relates to the first embodiment and is a perspective view of the channel operation mechanism at the time when the treatment instrument channel is not reduced in diameter.
Figure 7:
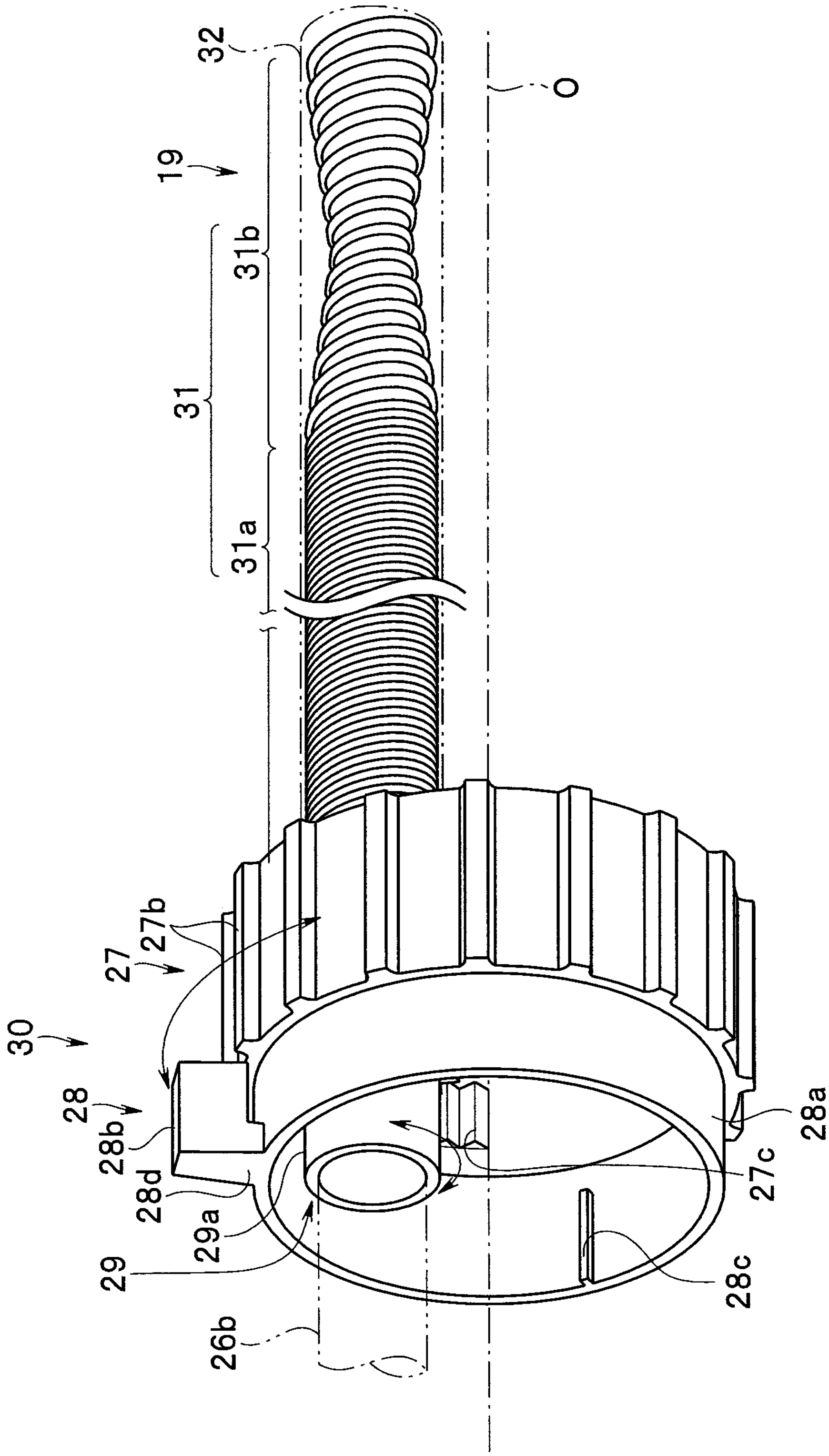
FIG. 7 relates to the first embodiment and is a perspective view of the channel operation mechanism at the time when the treatment instrument channel is reduced in diameter.
Figure 8:
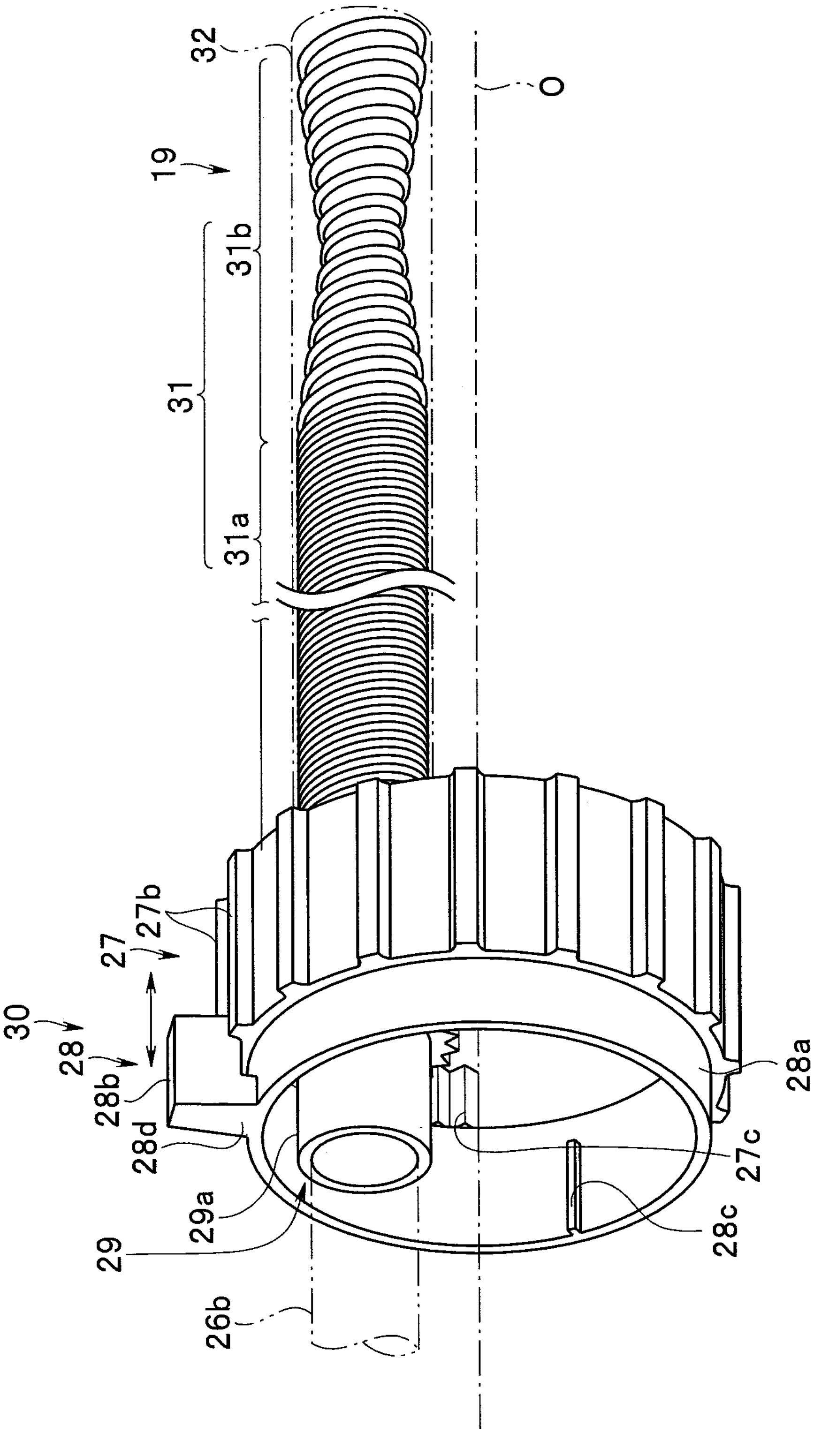
FIG. 8 relates to the first embodiment and is a perspective view of the channel operation mechanism at a time when the treatment instrument channel is reduced in diameter and locked.

As shown in FIG. 2 to FIG. 4, the channel operation mechanism 30 includes the channel operation knob 27, the slider 28, and a movable tube 29.

The channel operation knob 27 includes a knob main body 27*a* formed in a cylindrical shape, a plurality of ribs 27*b* projecting from an outer circumferential surface of the knob main body 27*a*, and a rack gear 27*c* provided on an inner circumferential surface of the knob main body 27*a*.

The knob main body 27*a* is fit on a first outer circumferential surface 35*a* formed in a frame 35 of the operation section 6. By the fitting, the knob main body 27*a* is supported by the operation section 6 in a state in which the knob main body 27*a* is turnable around the insertion axis O.

The plurality of ribs 27*b* are respectively extended in the axial direction of the insertion axis O. The respective ribs 27*b* are disposed at each equal interval on the outer circumferential surface of the knob main body 27*a*.

The rack gear 27*c* extends around the insertion axis O along the inner circumferential surface of the knob main body 27*a*. For example, the rack gear 27*c* is projected to the inside of the operation section 6 via a slit formed in the frame 35.

The slider 28 includes a slider main body 28*a* formed in a cylindrical shape and a lock member 28*b*.

The slider main body 28*a* has, for example, an outer diameter smaller than an inner diameter of the knob main body 27*a*. A key 28*c* extending in the axial direction of the insertion axis O is provided on an inner circumferential surface of the slider main body 28*a*.

The slider main body 28*a* is fit on a second outer circumferential surface 35*b* formed in the frame 35. The second outer circumferential surface 35*b* is formed in a position adjacent to the first outer circumferential surface 35*a* on the proximal end side of the frame 35. A key groove 35*d* extending in the axial direction of the insertion axis O is provided on the second outer circumferential surface 35*b*.

The key 28*c* of the slider main body 28*a* is engaged in the key groove 35*d*. Consequently, the slider main body 28*a* is capable of advancing and retracting between an advancing position (see FIG. 3) and a retracting position (see FIG. 2) in a state in which turning with respect to the operation section 6 is restricted. The advancing position is a position where the slider main body 28*a* advances to an inner circumference side of the knob main body 27*a*. The retracting position is a position where the slider main body 28*a* retracts from the inner circumference side of the knob main body 27*a*.

The lock member 28*b* is supported by the slider main body 28*a* via a supporting member 28*d* projecting from an outer circumferential surface of the slider main body 28*a*. Consequently, the lock member 28*b* is disposed in a position separated from the outer circumferential surface of the slider main body 28*a*.

The lock member 28*b* is inserted between a pair of ribs 27*b* on an outer circumference side of the channel operation knob 27 when the slider main body 28*a* moves to the advancing position. Consequently, the lock member 28*b* restricts turning of the channel operation knob 27.

On the other hand, the lock member 28*b* separates from the pair of ribs 27*b* when the slider main body 28*a* moves to the retracting position. Consequently, the lock member 28*b* allows the turning of the channel operation knob 27.

The movable tube 29 includes a tube main body 29*a* formed in a cylindrical shape and a pinion gear 29*b* provided in an outer circumference of the tube main body 29*a*.

The distal end side of the tube main body 29*a* is liquid-tightly connected to the proximal end side of the treatment instrument channel 19 in an unturnable state.

On the other hand, the proximal end side of the tube main body 29*a* is turnably supported with respect to the relay member 26.

For example, as shown in FIGS. 2 and 3, the relay member 26 includes, for example, a first branch tube 26*a*, a second branch tube 26*b*, and a third branch tube 26*c*. By including the first to third branch tubes 26*a* to 26*c*, the relay member 26 is configured by a rigid branch tube having a three-pronged structure. More specifically, in the relay member 26 in the present embodiment, the first branch tube 26*a* is connected to the pipe sleeve 25, the second branch tube 26*b* is connected to the treatment instrument channel 19, and the third branch tube 26*c* is connected to the suction button 22 via a suction tube 22*a*. The second branch tube 26*b* is extended in parallel to the insertion axis O, for example, in a position deviating in a predetermined direction (a direction in which the rack gear 27*c* is disposed) with respect to the insertion axis O.

The proximal end side of the tube main body 29*a* is liquid-tightly connected to the second branch tube 26*b* in a turnable state. By the connection, the second branch tube 26*b* turnably supports the proximal end side of the treatment instrument channel 19.

When the tube main body 29*a* is connected to the second branch tube 26*b*, the pinion gear 29*b* meshes with the rack gear 27*c* of the channel operation knob 27. Consequently, a rotational force of the channel operation knob 27 is transmitted to the proximal end side of the treatment instrument channel 19 via the movable tube 29.

When a rotational force in the winding direction of the coil 31 is transmitted to the proximal end side of the treatment instrument channel 19, the rotational force acts more strongly on the second coil section 31*b* side on which the element wire is roughly wound than the first coil section 31*a*. Consequently, the inner diameter of the second coil section 31*b* is elastically deformed in a diameter reducing direction. In other words, in a part further on the distal end side than the flexible tube section 12 of the insertion section 5, a sectional area of the inside of the treatment instrument channel 19 in the direction crossing the insertion axis O changes in the diameter reducing direction.

On the other hand, when a rotational force in an opposite direction of the winding direction of the coil 31 is transmitted to the proximal end side of the treatment instrument channel 19, the reduced inner diameter of the second coil section 31*b* is restored in a diameter expanding direction. In other words, in a part further on the distal end side than the flexible tube section 12 of the insertion section 5, the sectional area of the inside of the treatment instrument channel 19 in the direction crossing the insertion axis O changes in the diameter expanding direction.

Figure 9:
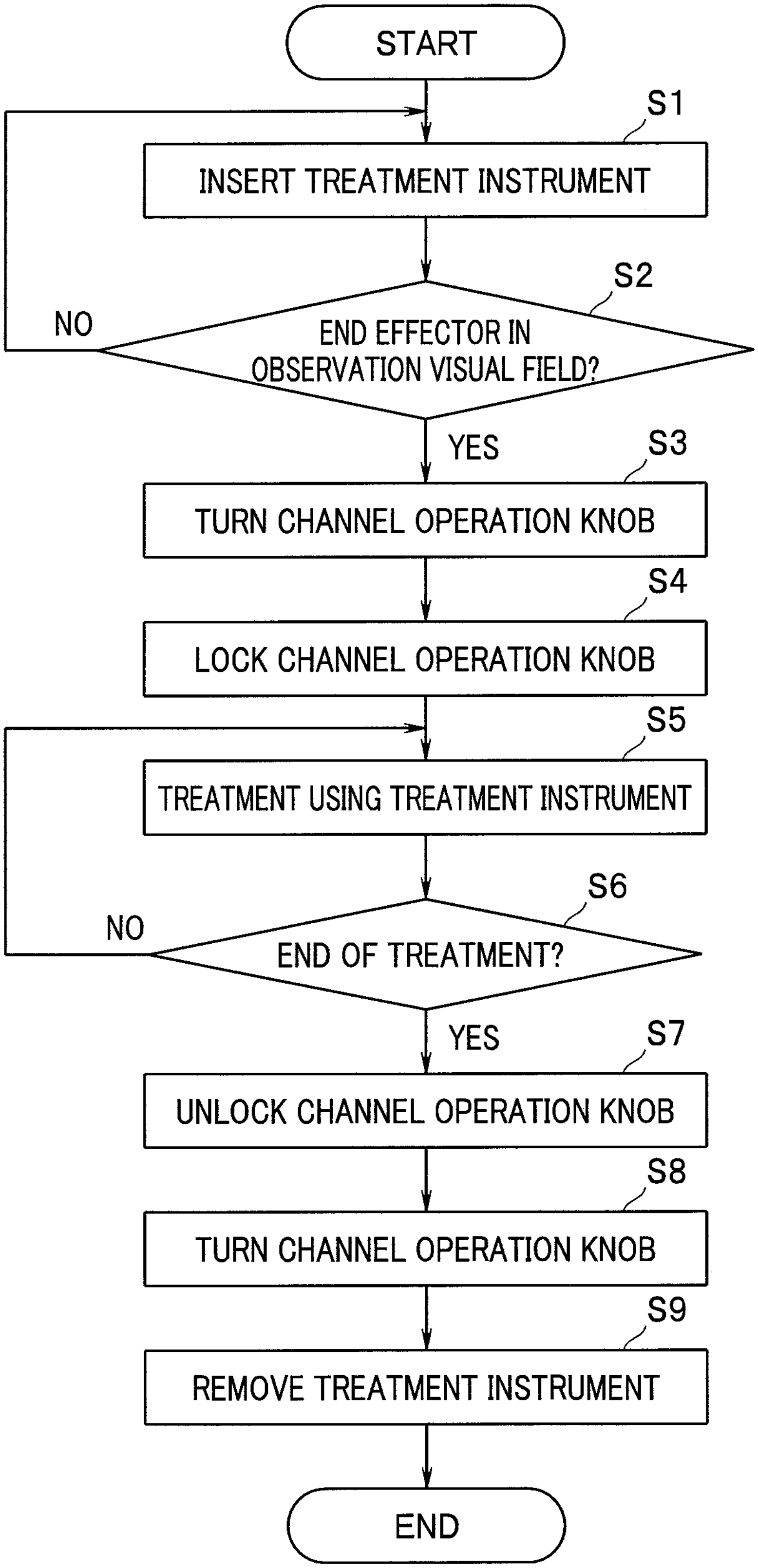
FIG. 9 relates to the first embodiment and is a flowchart showing a positioning method for a treatment instrument.
Figure 10:
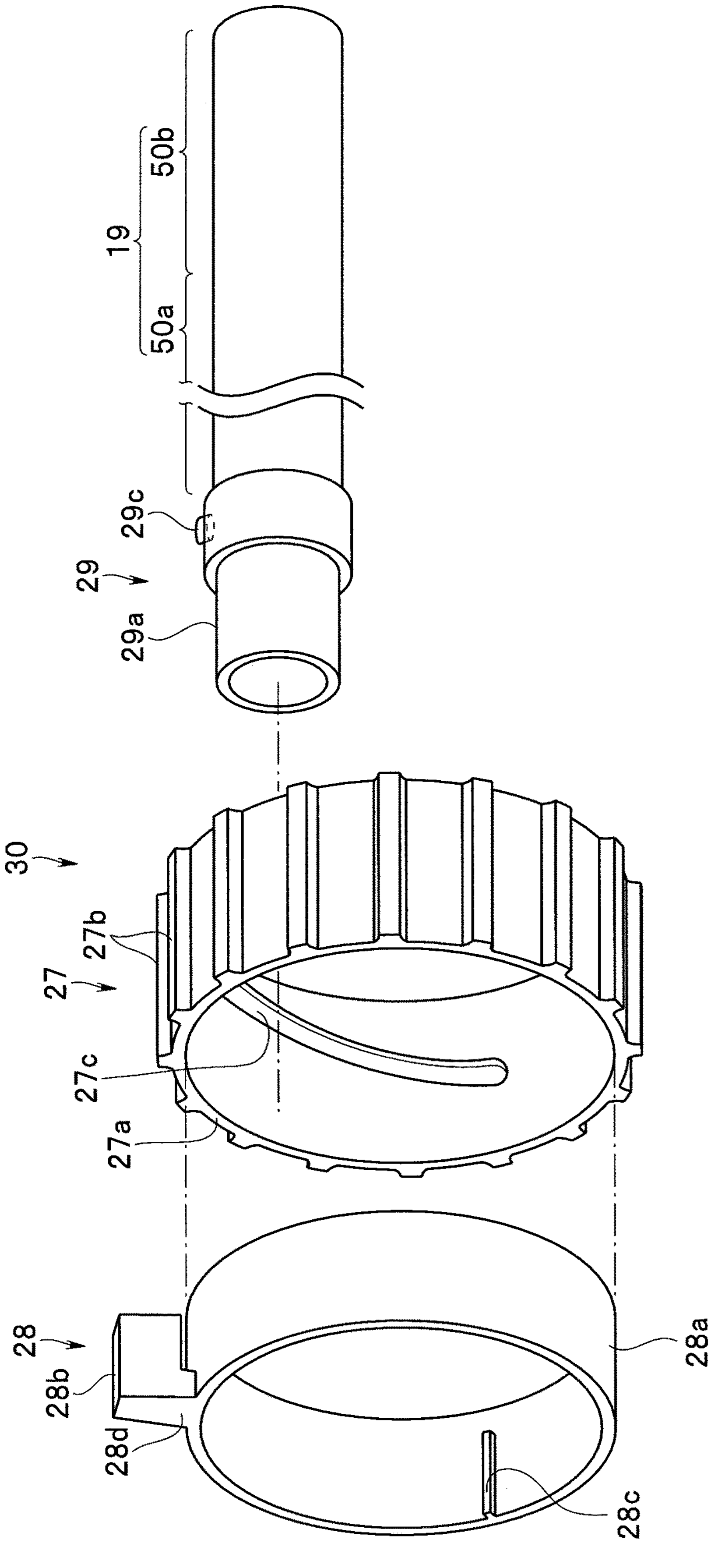
FIG. 10 relates to a second embodiment and is an exploded perspective view of a channel operation mechanism.
Figure 11:
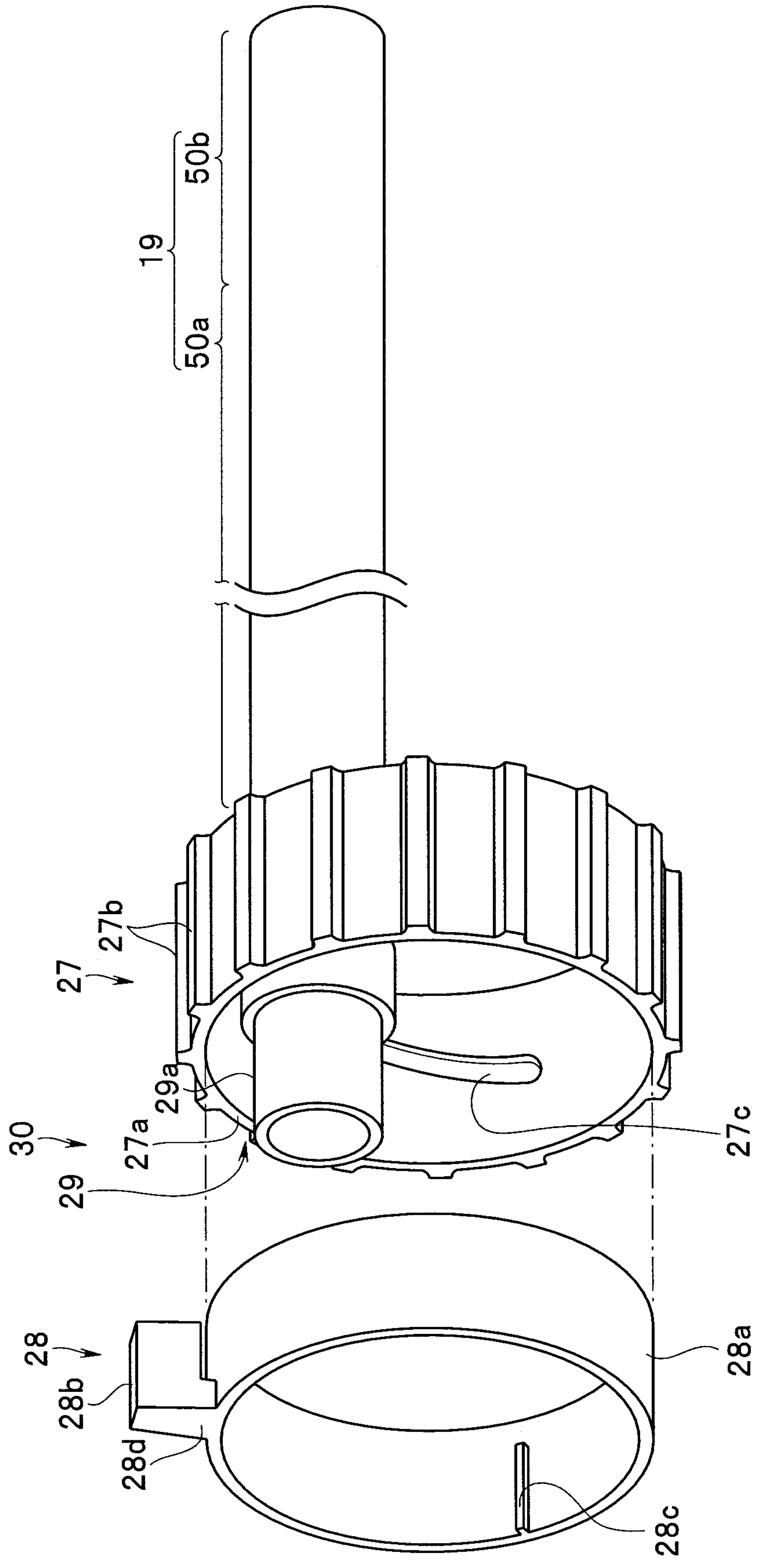
FIG. 11 relates to the second embodiment and is a perspective view of the channel operation mechanism from which a slider is detached.
Figure 12:
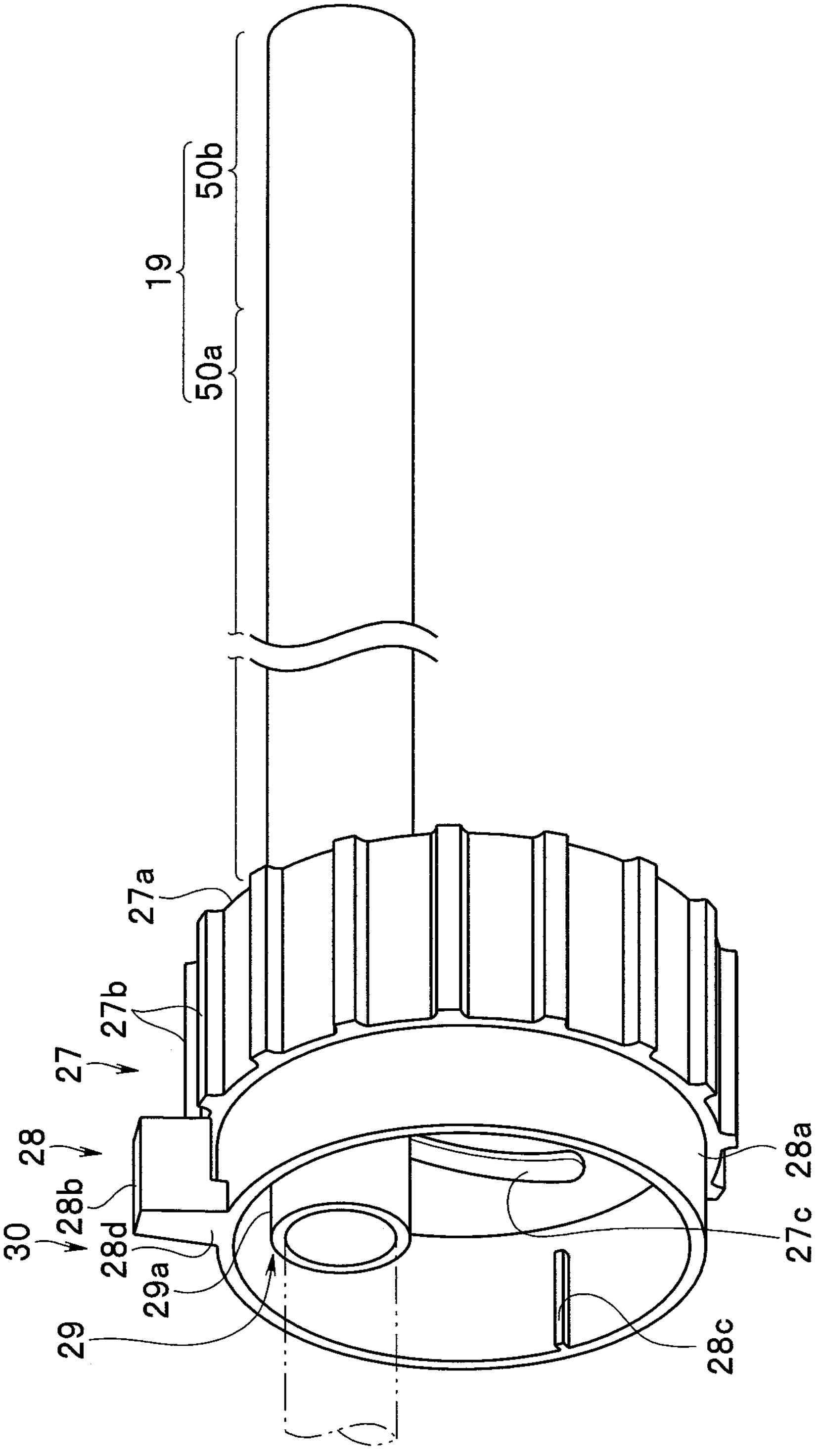
FIG. 12 relates to the second embodiment and is a perspective view of the channel operation mechanism at a time when a treatment instrument channel is not reduced in diameter.
Figure 13:
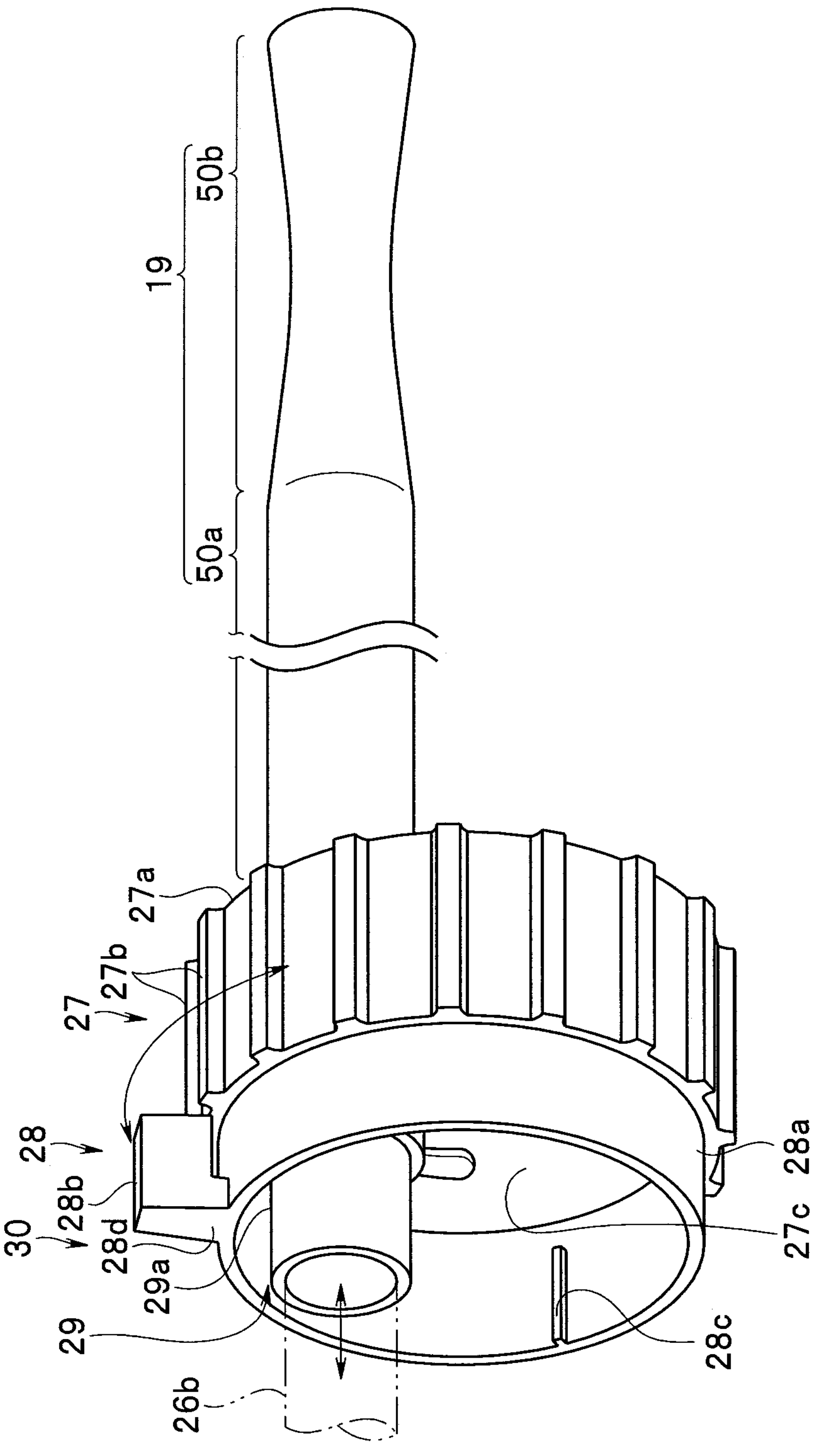
FIG. 13 relates to the second embodiment and is a perspective view of the channel operation mechanism at a time when the treatment instrument channel is reduced in diameter.
Figure 14:
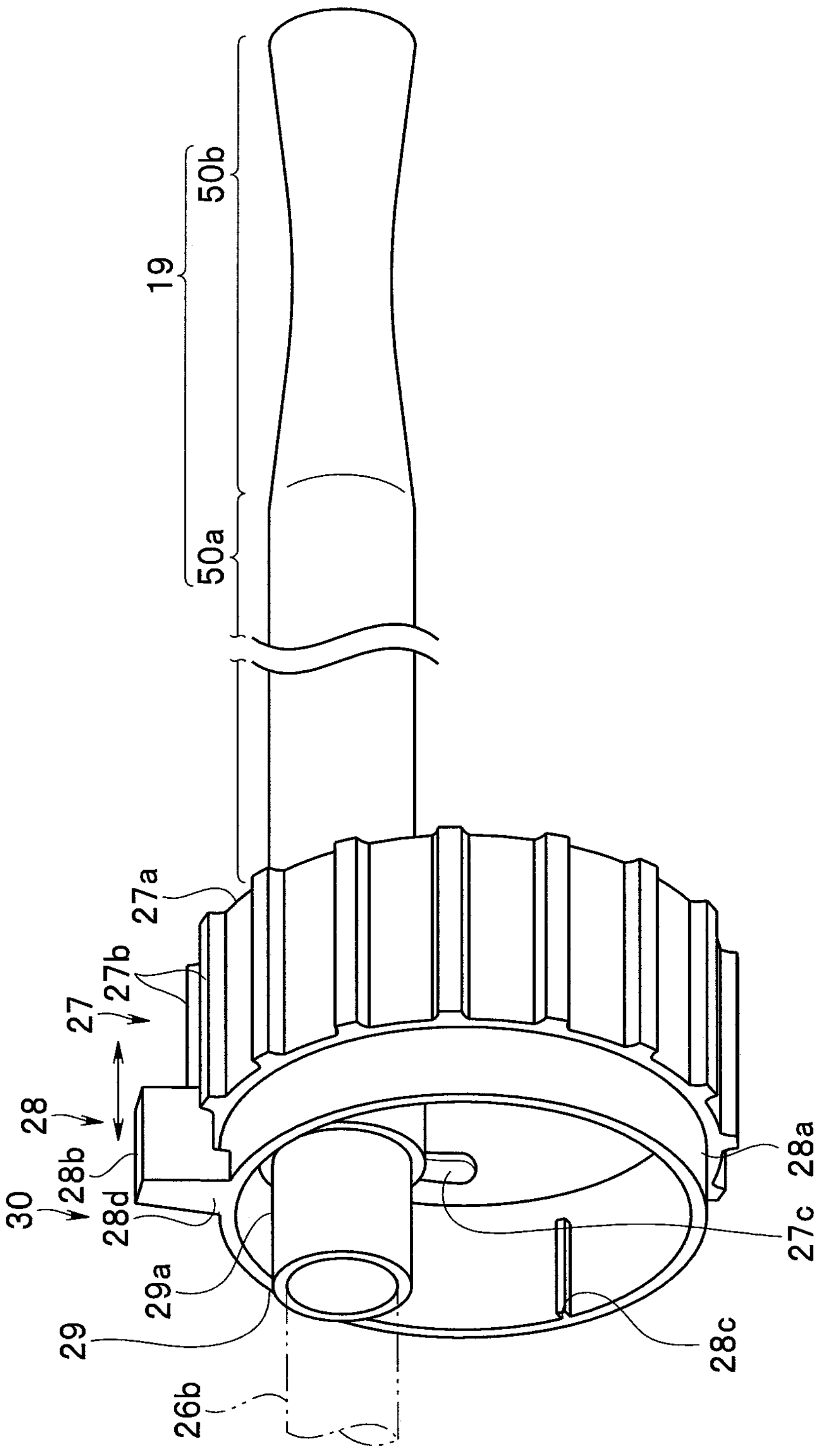
FIG. 14 relates to the second embodiment and is a perspective view of the channel operation mechanism at a time when the treatment instrument channel is reduced in diameter and locked.

Subsequently, a positioning method for the treatment instrument 8 using the endoscope 1 configured as explained above is explained with reference to a flowchart of FIG. 9.

In positioning of the treatment instrument 8, the surgeon or the like inserts the treatment instrument 8 into the inside of the treatment instrument channel 19 via the pipe sleeve 25 of the operation section 6 (step S1). Insertion work for the treatment instrument 8 is performed up to at least a position where the end effector 8*a* of the treatment instrument 8 moves further to the distal end side than the second coil section 31*b* of the treatment instrument channel 19 (see FIG. 2). For example, the insertion work for the treatment instrument 8 is performed up to a position where the end effector 8*a* of the treatment instrument 8 intrudes into an observation visual field of the image pickup unit 16.

The end effector 8*a* of the treatment instrument 8 intrudes into the observation visual field of the image pickup unit 16 (step S2: YES).

Thereafter, the surgeon or the like turns the channel operation knob 27 in the normal direction of the winding direction of the coil 31 (step S3).

A rotational force on the channel operation knob 27 is transmitted to the proximal end side of the treatment instrument channel 19 via the rack gear 27*c* and the pinion gear 29*b*. Consequently, the rotational force in a twisting (squeezing) direction is transmitted to the second coil section 31*b*. The inner diameter of the second coil section 31*b* (that is, the inner diameter of the treatment instrument channel 19) is reduced (see FIGS. 3 and 7).

The surgeon or the like locks a rotation position of the channel operation knob 27 (step S4). In other words, the surgeon or the like moves the slider 28 to the channel operation knob 27 side and inserts the lock member 28*b* between the pair of ribs 27*b*. Consequently, even after the surgeon or the like releases a hand from the channel operation knob 27, a state in which the inner diameter of the second coil section 31*b* is reduced is maintained.

By the reduction of the inner diameter of the second coil section 31*b*, the shaft 8*b* of the treatment instrument 8 is positioned closer to a center of the inside of the treatment instrument channel 19 on the distal end side of the insertion section 5. Consequently, even when the inner diameter of the treatment instrument channel 19 is sufficiently larger than the outer diameter of the shaft 8*b* of the treatment instrument 8, a bend of the shaft 8*b* is corrected on the distal end side of the insertion section 5. Therefore, behavior of the end effector 8*a* is stabilized. It is easy for the end effector 8*a* to access a target site in the subject.

Thereafter, treatment using the treatment instrument 8 is performed by the surgeon or the like (step S5). When the treatment ends (step S6: YES), the surgeon or the like unlocks the channel operation knob 27 (step S7). In other words, the surgeon or the like moves the slider 28 to the opposite side of the channel operation knob 27 and retracts the lock member 28*b* from between the pair of ribs 27*b*.

The surgeon or the like turns the channel operation knob 27 in the opposite direction of the winding direction of the coil 31 (step S8). A rotational force on the channel operation knob 27 is transmitted to the proximal end side of the treatment instrument channel 19 via the rack gear 27*c* and the pinion gear 29*b*. Consequently, a rotational force in a direction in which a twist is reduced (a squeeze is released) is transmitted to the second coil section 31*b*. The inner diameter of the second coil section 31*b* (that is, the inner diameter of the treatment instrument channel 19) expands to the original inner diameter (see FIGS. 2 and 6).

Thereafter, the surgeon or the like removes the treatment instrument 8 from the treatment instrument channel 19 (step S9). At this time, since the inner diameter of the second coil section 31*b* is expanded to the original inner diameter, it is possible to easily remove the treatment instrument 8 from the treatment instrument channel 19.

Such an endoscope 1 in the embodiment includes the treatment instrument channel 19 provided on the inside of the insertion section 5 along the insertion axis O extending from the proximal end to the distal end of the insertion section 5, the treatment instrument 8 being inserted through the treatment instrument channel 19, and the channel operation knob 27 that transmits an operation force to the treatment instrument channel 19. The treatment instrument channel 19 includes the second coil section 31*b* that changes, according to operation on the channel operation knob 27, the sectional area of the inside of the treatment instrument channel 19 in the direction crossing the insertion axis O. With these components, it is possible to improve operability of the treatment instrument 8 inserted through the treatment instrument channel 19.

In other words, by reducing the inner diameter on the distal end side of the treatment instrument channel 19, it is possible to position the shaft 8*b* of the treatment instrument 8 closer to the center of the treatment instrument channel 19 on the distal end side of the insertion section 5. Therefore, even when the inner diameter of the treatment instrument channel 19 is sufficiently larger than the outer diameter of the shaft 8*b*, it is possible to correct a bend of the shaft 8*b* and improve operability of the treatment instrument 8.

The treatment instrument channel 19 adopts a configuration in which the outer skin 32 covers the outer circumference of the coil 31. However, the treatment instrument channel 19 may adopt a configuration in which a flexible resin tube is provided on an inner side of the coil 31 instead of the outer skin 32. In other words, an inner skin may be formed on the coil 31 instead of the outer skin 32. In this case as well, it is possible to obtain the same effects while securing watertightness of the treatment instrument channel 19.

Subsequently, a second embodiment is explained with reference to FIG. 10 to FIG. 14. In the first embodiment explained above, the configuration is explained in which the inner diameter of the treatment instrument channel 19 is reduced by applying a force in the twisting direction to the treatment instrument channel 19. In contrast, in the present embodiment, a configuration is explained in which an inner diameter of the treatment instrument channel 19 is reduced by applying a force in a towing direction to the treatment instrument channel 19. Note that the same components as the components in the embodiment explained above are denoted by the same reference numerals and signs and explanation of the components is omitted as appropriate.

As shown in FIG. 10 to FIG. 14, in the present embodiment, the treatment instrument channel 19 is configured by, for example, a tube made of resin. The treatment instrument channel 19 includes a first tube section 50*a* and a second tube section 50*b* functioning as an elastic member.

The first tube section 50*a* is disposed, for example, on an inside of the operation section 6 and an inside of the flexible tube section 12.

The second tube section 50*b* is continuously formed on a distal end side of the first tube section 50*a*. The second tube section 50*b* has more flexibility than the first tube section 50*a*. The flexibility of the second tube section 50*b* can be realized by, for example, forming the second tube section 50*b* thinner than the first tube section 50*a*. Alternatively, the flexibility of the second tube section 50*b* can be realized by two-color molding the treatment instrument channel 19 with a resin material different from a material of the first tube section 50*a*. The second tube section 50*b* formed in this way is disposed, for example, on insides of the bending section 11 and the distal end portion 10.

The channel operation knob 27 configuring the channel operation mechanism 30 includes a cam groove 27*d* on an inner circumferential surface instead of the rack gear 27*c*.

The cam groove 27*d* is inclined at a predetermined angle with respect to the insertion axis O.

A proximal end side of the tube main body 29*a* configuring the movable tube 29 is liquid-tightly connected to the second branch tube 26*b* in a state in which the tube main body 29*a* is capable of advancing and retracting in the insertion axis O direction.

A pin 29*c* is provided in an outer circumference of the tube main body 29*a* instead of the pinion gear 29*b*. The pin 29*c* is engaged in the cam groove 27*d* when the tube main body 29*a* is connected to the second branch tube 26*b*.

By the engagement, when the channel operation knob 27 is operated around the insertion axis O, a rotational force of the channel operation knob 27 is converted into a force in the axial direction of the insertion axis O and, thereafter, transmitted to the movable tube 29.

In other words, according to a turning direction of the channel operation knob 27, the movable tube 29 advances and retracts in a direction in which the treatment instrument channel 19 is towed or slacked.

When a force in the towing direction is transmitted to the treatment instrument channel 19 via the movable tube 29, the second tube section 50*b* extends in the axial direction of the insertion axis O. By the extension, an inner diameter of the second tube section 50*b* is reduced (see FIG. 13). Note that, by moving the slider 28 to the channel operation knob 27 side and inserting the lock member 28*b* between the pair of ribs 27*b*, it is possible to maintain a reduced diameter state of the second tube section 50*b* (see FIG. 14).

On the other hand, when the towing of the treatment instrument channel 19 by the movable tube 29 is slacked, the second tube section 50*b* contracts in the axial direction of the insertion axis O. By the contraction, the inner diameter of the second tube section 50*b* is expanded to an original inner diameter (see FIG. 12).

According to such an embodiment, it is possible to achieve substantially the same effects as the effects in the first embodiment explained above.

Note that the present disclosure is not limited to the respective embodiments explained above and various modifications and changes are possible. The modifications and the changes are also within a technical scope of the present disclosure.

For example, in the respective embodiments explained above, the configuration of the endoscope is explained as an example of the medical apparatus. However, the present disclosure is not limited to this. For example, the present disclosure can also be applied to an over-tube functioning as the medical apparatus. In other words, it is possible to achieve substantially the same effects as the effects in the respective embodiments by applying the treatment instrument channel in the respective embodiments to a treatment instrument channel of the over-tube.

In the respective embodiments explained above, the configuration of the single-use endoscope is explained as an example of the endoscope. However, it goes without saying that the endoscope is not limited to the single-use endoscope.

It goes without saying that the configurations of the respective embodiments explained above may be combined as appropriate.

1. A medical apparatus comprising:

an insertion section inserted into a subject;

a treatment instrument channel provided in the insertion section along an insertion axis extending from a proximal end to a distal end of the insertion section, a treatment instrument being inserted through the treatment instrument channel;

an elastic member provided in at least a part of the treatment instrument channel; and a channel operation member for transmitting an operation force to the elastic member, wherein the elastic member changes, according to the operation force, a sectional area of an inside of the treatment instrument channel in a direction crossing the insertion axis.

2. The medical apparatus according to example 1, wherein the elastic member is deformed according to the operation force, and the sectional area of the treatment instrument channel changes when the elastic member is deformed.

3. The medical apparatus according to example 1, wherein the direction crossing the insertion axis is a direction orthogonal to the insertion axis.

4. The medical apparatus according to example 2, wherein the channel operation member transmits turning operation around the insertion axis to the treatment instrument channel.

5. The medical apparatus according to example 2, wherein the elastic member is a coil on which an element wire is wound, and the coil changes the sectional area of the inside of the treatment instrument channel when a rotational force in a normal direction or an opposite direction with respect to the winding direction is transmitted to the coil according to the operation force.

6. The medical apparatus according to example 2, wherein the elastic member is a resin tube, and the resin tube changes the sectional area of the inside of the treatment instrument channel when the resin tube is towed or slacked in the insertion axis direction according to the operation force.

7. The medical apparatus according to example 4, further comprising a fixing member capable of fixing a turning position of the channel operation member.

8. The medical apparatus according to example 1, wherein the insertion section includes a distal end portion including an opening for leading out the treatment instrument inserted through the treatment instrument channel, a bending section provided at a proximal end of the distal end portion, and a flexible tube section provided at a proximal end of the bending section, and the elastic member is provided further on a distal end side than the flexible tube section.

9. The medical apparatus according to example 1, further comprising:

an illumination unit configured to illuminate the subject; and an image pickup unit configured to pick up an image of the subject.

10. A medical apparatus comprising:

an insertion section inserted into a subject;

a treatment instrument channel provided in the insertion section along an insertion axis extending from a proximal end to a distal end of the insertion section, a treatment instrument being inserted through the treatment instrument channel;

an elastic member provided in at least a part of the treatment instrument channel; and a channel operation member for transmitting an operation force in a twisting direction or a towing direction to the treatment instrument channel, wherein the elastic member is deformed by the operation force in the twisting direction or the towing direction and reduces a sectional area of an inside of the treatment instrument channel in a direction crossing the insertion axis.

11. A positioning method for a treatment instrument using the medical apparatus according to example 1, the positioning method comprising:

inserting the treatment instrument to a predetermined position of the treatment instrument channel; and operating the channel operation member and reducing the sectional area of at least a part of the inside of the treatment instrument channel.

12. The positioning method for the treatment instrument according to example 11, wherein the treatment instrument channel is reduced in diameter partway along a longitudinal axis.

13. The positioning method for the treatment instrument according to example 11, wherein the sectional area of at least the part of the inside of the treatment instrument channel is reduced by transmitting an operation force in a twisting direction or a towing direction to the treatment instrument channel.

14. The positioning method for the treatment instrument according to example 13, wherein the operation force in the twisting direction or the towing direction is transmitted to the treatment instrument channel by turning the channel operation member.

15. The positioning method for the treatment instrument according to example 11, wherein the predetermined position is a position where an end effector of the treatment instrument is disposed further on a distal end side than a position where the sectional area is reduced.

16. The positioning method for the treatment instrument according to example 11, wherein the predetermined position is a position where an end effector of the treatment instrument is disposed within a visual field of an image pickup unit disposed at the distal end of the insertion section.

What is claimed is:

1. A medical apparatus, comprising:

an insertion section;

a treatment instrument channel located in the insertion section, the treatment instrument channel including a coil formed by a wound element wire; and a treatment instrument insertable into the treatment instrument channel, wherein the coil forms an inner diameter surface of the treatment instrument channel, wherein the treatment instrument channel is configured to be deformed by an operational force, wherein in response to the operational force transmitted to the treatment instrument channel, the coil changes a cross-sectional area of the treatment instrument channel in a direction intersecting an axis of the treatment instrument channel, wherein the treatment instrument channel further includes a channel operation member coupled to the coil for transmitting the operational force to the coil, wherein the channel operation member is rotatable relative to the treatment instrument channel around the axis, wherein a rotation of the channel operation member relative to the treatment instrument channel around the axis transmits the operational force to the treatment instrument channel, wherein the insertion section includes:

a distal end portion including an opening for leading out the treatment instrument inserted through the treatment instrument channel, a bending section provided at a proximal end of the distal end portion, and a flexible tube section provided at a proximal end of the bending section, and wherein the coil is provided distally relative to the flexible tube section and deforms to change the cross-sectional area of the treatment instrument channel.

2. The medical apparatus according to claim 1, wherein the direction intersecting the axis is a perpendicular to the axis.

3. The medical apparatus according to claim 1, further comprising a lock.

4. The medical apparatus according to claim 1, further comprising:

an illumination unit configured to illuminate an operation site, and an image pickup sensor configured to obtain an image of the operation site.

5. A medical apparatus, comprising:

an insertion section;

a treatment instrument channel located in the insertion section;

a treatment instrument insertable into the treatment instrument channel;

a coil formed by a wound element wire and located in at least a part of the treatment instrument channel; and a channel operation member coupled to the treatment instrument channel for transmitting an operational force to the coil, wherein the coil forms an inner diameter surface of the treatment instrument channel, wherein, in response to the operational force transmitted to the coil by the channel operation member, the coil changes a cross-sectional area of an inside of the treatment instrument channel in a direction intersecting an axis of the treatment instrument channel, wherein the treatment instrument channel further includes a channel operation member coupled to the coil for transmitting the operational force to the coil, wherein the channel operation member is rotatable relative to the treatment instrument channel around the axis, wherein a rotation of the channel operation member relative to the treatment instrument channel around the axis transmits the operational force to the treatment instrument channel, wherein the insertion section includes:

a distal end portion including an opening for leading out the treatment instrument inserted through the treatment instrument channel, a bending section provided at a proximal end of the distal end portion, and a flexible tube section provided at a proximal end of the bending section, and wherein the coil is provided distally relative to the flexible tube section and deforms to change the cross-sectional area of the treatment instrument channel.

6. A method for positioning a treatment instrument using the medical apparatus according to claim 1, the method comprising:

inserting the treatment instrument to a predetermined position of the treatment instrument channel; and changing the cross-sectional area of the treatment instrument channel in the direction intersecting the axis of the treatment instrument channel.

7. The method according to claim 6, wherein changing the cross-sectional area of the treatment instrument channel includes reducing a diameter partway along a longitudinal axis of the treatment instrument channel.

8. The method according to claim 6, wherein changing the cross-sectional area of the treatment instrument channel includes reducing the cross-sectional area of at least a part of the treatment instrument channel.

9. The method according to claim 8, wherein the operational force is a force in a twisting direction or in a towing direction.

10. The method according to claim 9, wherein the method further comprises moving a first part of the treatment instrument channel relative to a second part of the treatment instrument channel around the axis of the treatment instrument channel to transmit the operational force to the second part of the treatment instrument channel.

11. The method according to claim 6, wherein the treatment instrument includes an end effector, and wherein the predetermined position is a position where the end effector is located distally relative to a position where the cross-sectional area is changed.

12. The method according to claim 6, wherein the medical apparatus further comprises an image pickup sensor having a field of view, wherein the image pickup sensor is located at a distal end of the insertion section, wherein the treatment instrument includes an end effector, and wherein the predetermined position is a position where the end effector is located within the field of view.

13. The medical apparatus according to claim 1, wherein the channel operation member is a ring.

14. The medical apparatus according to claim 1, further comprising:

an operation section, wherein the treatment instrument channel extends from a proximal end located in the operation section to a distal end located in the insertion section, and wherein, in response to the operational force transmitted to the coil by the channel operation member, the coil is configured to deform to change the cross-sectional area of the treatment instrument channel in the direction intersecting the axis.

15. The medical apparatus according to claim 1, wherein the coil is configured to deform to change the cross-sectional area of the treatment instrument channel, and wherein the deformed coil has a tapered shape.

16. The medical apparatus according to claim 1, further comprising:

a first gear provided on an inner circumferential surface of an operation knob; and a second gear provided on an outer circumference of the treatment instrument channel to transmit the operational force to the treatment instrument channel from the operation knob.

17. The medical apparatus according to claim 1, wherein the treatment instrument channel further includes an outer skin that covers an outer circumference of the coil.

* * * * *